(12) United States Patent
Andreasson

(10) Patent No.: US 11,698,343 B2
(45) Date of Patent: Jul. 11, 2023

(54) MOLECULAR CONSTRUCT FOR MULTIPHOTON FLUORESCENCE MICROSCOPY IMAGING

(71) Applicant: Joakim Andreasson, Landvetter (SE)

(72) Inventor: Joakim Andreasson, Landvetter (SE)

(73) Assignee: Joakim Andreasson, Landvetter (SE)

( * ) Notice: Subject to any disclaimer, the term of this patent is extended or adjusted under 35 U.S.C. 154(b) by 191 days.

(21) Appl. No.: 17/220,155

(22) Filed: Apr. 1, 2021

(65) Prior Publication Data

US 2022/0155231 A1    May 19, 2022

(30) Foreign Application Priority Data

Nov. 18, 2020   (SE) .................................... 2051344-6

(51) Int. Cl.
*G01N 21/64* (2006.01)
*G02B 21/00* (2006.01)
*G02B 21/16* (2006.01)

(52) U.S. Cl.
CPC ..... *G01N 21/6486* (2013.01); *G01N 21/6428* (2013.01); *G01N 21/6458* (2013.01);
(Continued)

(58) Field of Classification Search
CPC ........... G01N 21/6486; G01N 21/6428; G01N 21/6458; G01N 2021/6432; G01N 2201/06113; G02B 21/0076
See application file for complete search history.

(56) References Cited

U.S. PATENT DOCUMENTS 6,566,529 B1 *  5/2003  Kim .................... C07D 495/14
                                                    548/444
7,253,287 B1 *  8/2007  Belfield .............. C07D 277/66
                                                    548/160
(Continued)

FOREIGN PATENT DOCUMENTS

CN           107082775 B      7/2019

OTHER PUBLICATIONS

Yamaguchi, Tetsuo, Yoichi Kobayashi, and Jiro Abe. "Fast negative photochromism of 1, 1'-binaphthyl-bridged phenoxyl-imidazolyl radical complex." Journal of the American Chemical Society 138.3 (2016): 906-913. (Year: 2016).*

(Continued)

*Primary Examiner* — Dominic J Bologna
(74) *Attorney, Agent, or Firm* — Kilpatrick Townsend and Stockton LLP

(57) ABSTRACT

The present disclosure generally relates to a molecular construct for multiphoton fluorescence microscopy imaging. The molecular construct has a first, non-fluorescent configuration (2PAP-C) and a second, fluorescent configuration (2PAP-CL), and comprises a two-photon absorbing probe (2PAP) linked to a photochromic molecule that can be reversibly changed from a first colored isomeric form (C) to a second colorless isomeric form (CL). The first colored form (C) can be isomerized to the second colorless isomeric form (CL) upon absorption of two photons by the two-photon absorbing probe (2PAP). The present disclosure also relates to a method for analyzing a target structure in a multiphoton microscope utilizing the molecular construct. Furthermore, the present disclosure relates to an antibody tagged with the molecular construct, and to the use of the molecular construct for imaging a target structure.

20 Claims, 4 Drawing Sheets

(52) U.S. Cl.
CPC ......... *G02B 21/0076* (2013.01); *G02B 21/16* (2013.01); *G01N 2021/6432* (2013.01); *G01N 2201/06113* (2013.01)

(56) References Cited

U.S. PATENT DOCUMENTS

| | | | |
|---|---|---|---|
| 9,255,933 B2* | 2/2016 | Guo | A61K 49/0026 |
| 2005/0019954 A1* | 1/2005 | Shukla | G01N 33/585 |
| | | | 436/518 |
| 2015/0343102 A1* | 12/2015 | Romo | A61L 2/10 |
| | | | 436/1 |

OTHER PUBLICATIONS

Benitez-Martin, Carlos, et al. "Toward two-photon absorbing dyes with unusually potentiated nonlinear fluorescence response." Journal of the American Chemical Society 142.35 (2020): 14854-14858. (Year: 2020).*

Zhu, Ming-Qiang, et al. "Reversible two-photon photoswitching and two-photon imaging of immunofunctionalized nanoparticles targeted to cancer cells." Journal of the American Chemical Society 133.2 (2011): 365-372. (Year: 2011).*

C. Benitez-Martin et al., "Toward Two-Photon Absorbing Dyes with Unusually Potentiated Nonlinear Fluorescence Response", J. Am. Chem. Soc., No. 142, pp. 14854-14858 (2020).

International Application No. PCT/SE2021/051135, International Search Report dated Jan. 4, 2022, 18 pages.

L. Bekere et al., "Chromenes involving a two-photon absorbing moiety: photochromism via intramolecular resonance energy transfer", New J. Chem., vol. 40, pp. 1143-1148 (2016).

M. Li et al., "A novel multiphotochromic system with orthogonal light excitations", Dyes and Pigments, vol. 166, pp. 239-244 (2019).

T. Senthilkumar et al., "Conjugated Polymer Nanoparticles with Appended Photo-Responsive Units for Controlled Drug Delivery, Release and Imaging", Angew. Chem. Int. Ed., vol. 57, pp. 13114-13119 (2018).

T. Yamaguchi et al., "Fast Negative Photochromism of 1,1'-Binaphthyl-Bridged Phenoxyl-Imidazolyl Radical Complex", J. Am. Chem. Soc., vol. 138, pp. 906-913 (2016).

M. Zhu et al., "Reversible Two-Photon Photoswitching and Two-Photon Imaging of Immunofunctionalized Nanoparticles Targeted to Cancer Cells", J. Am. Chem. Soc., vol. 133, pp. 365-372 (2011).

Swedish Application No. 2051344-6, Office Action dated Jun. 15, 2021, 8 pages.

Swedish Application No. 2051344-6, Search Report dated Jun. 15, 2021, 1 page.

* cited by examiner

MOLECULAR CONSTRUCT FOR MULTIPHOTON FLUORESCENCE MICROSCOPY IMAGING

CROSS-REFERENCE TO RELATED APPLICATIONS

The present application claims the benefit of priority to SE Application No. 2051344-6, filed on Nov. 18, 2020, the entire contents of each of which are incorporated by reference herein.

TECHNICAL FIELD

The present disclosure generally relates to a molecular construct for multiphoton fluorescence microscopy imaging. The molecular construct has a first, non-fluorescent configuration (2PAP-C) and a second, fluorescent configuration (2PAP-CL), and comprises a two-photon absorbing probe (2PAP) linked to a photochromic molecule that can be reversibly changed from a first colored isomeric form (C) to a second colorless isomeric form (CL). The first colored form (C) can be isomerized to the second colorless isomeric form (CL) upon absorption of two photons by the two-photon absorbing probe (2PAP). The present disclosure also relates to a method for analyzing a target structure in a multiphoton microscope utilizing the molecular construct. Furthermore, the present disclosure relates to an antibody tagged with the molecular construct, and to the use of the molecular structure for imaging a target structure.

BACKGROUND

Multiphoton microscopy imaging allows for a sophisticated high-resolution visualization of various structures and biological samples. Such imaging allows for the visualization and analysis of the tissue morphology and physiology both in vivo and ex vivo at cellular level deep down in the tissue.

The most common multiphoton fluorescence imaging technique is two-photon microscopy, which utilizes two near-infrared photons as the excitation source. Two-photon excitation is a fluorescence process in which a fluorophore; i.e. a fluorescent probe, is excited by the simultaneous absorption of two photons.

Two-photon absorbing probes allow for deep tissue penetration, efficient light detection and reduced photobleaching, which makes the technique useful in various applications such as bioimaging, diagnosis and monitoring of diseases.

Two-photon excitation is a nonlinear optical process and requires simultaneous excitation by two photons with longer wavelength than the emitted light. Two-photon excitation microscopy typically utilizes near-infrared (NIR) excitation light, delivered by e.g. a laser, to excite fluorescent dyes. For each excitation, two photons of NIR light are absorbed. Since the process depends on the simultaneous absorption of two photons, the resulting fluorescence emission varies with the square of the excitation intensity.

When two-photon probes are applied in multiphoton microscopy, the intensity of the light displays a quadratic decrease with distance from the focal point, implying that two-photon absorbing probes emit light such that the fluorescence intensity varies as $1/z^4$, where z is the distance from the focal point. In multiphoton processes utilizing three-photon and four-photon absorbing probes, the fluorescence intensity may vary as $1/z^6$, and $1/z^8$, respectively.

Accordingly, the use of three- and four-photon absorbent probes may significantly increase the spatial resolution of the imaged sample. However, the use of three- and four-photon absorbent probes in multiphoton imaging applications typically requires extreme light intensities. This is due to the low probability for three, and four, respectively, photons to be absorbed simultaneously by the probe, and also due to hard-to access excitation wavelengths. This limits the use of three- and four photon probes in multiphoton microscopy applications.

Regardless of the molecular probe used for two-photon microscopy, the process is always limited by the fundamental law of photophysics; i.e. the emission intensity depends quadratically on the intensity of the excitation light, resulting in the $1/z^4$ resolution. The quadratic dependence on these molecules results from the mechanism of two-photon absorption; i.e. two photons are absorbed by the molecule such that the sum of the photon energies corresponds to the energy of the two-photon allowed electronic transition. As two photons are required to hit the molecule simultaneously, the probability (and rate) of photon absorption for each individual molecule depends quadratically on the photon flux.

In view of the above-mentioned challenges, there is a need to provide an improved probe for multiphoton microscopy applications, which combines the advantages associated with two-photon absorbing probes and three- or four photon absorbing probes. More specifically, there is a need to provide an improved two-photon absorbing probe that can provide for an enhanced spatial resolution of an imaged structure or sample.

SUMMARY

In view of the above mentioned problems, it is an object of the present disclosure to provide improvements with respect to multiphoton probes for use in multiphoton microscopy imaging. Particularly, there is a need to provide a two-photon absorbing probe capable of providing an improved spatial resolution.

According to a first aspect of the present disclosure, there is provided a molecular construct for multiphoton fluorescence microscopy imaging, wherein the molecular construct has a first, non-fluorescent configuration (2PAP-C) and a second, fluorescent configuration (2PAP-CL), wherein the molecular construct comprises
 a two-photon absorbing probe (2PAP) linked to
 a photochromic molecule, wherein the photochromic molecule can be reversibly changed from a first colored isomeric form (C) to a second colorless isomeric form (CL), wherein the first colored form (C) can be isomerized to the second colorless isomeric form (CL) upon absorption of two photons by the two-photon absorbing probe (2PAP), wherein the absorption spectrum of the first colored isomeric form (C) overlaps the emission spectrum of the two-photon absorbing probe (2PAP), and wherein the absorption spectrum of the second colorless isomeric form (CL) does not overlap the emission spectrum of the two-photon absorbing probe (2PAP).

The molecular construct of the present disclosure relies on the excitation by two-photon absorption, but may offer the same spatial resolution as a four-photon absorbing probe when used in two-photon microscopy. In other words, the molecular construct of the present disclosure combines the advantages of two-photon absorbing probes (relatively low excitation intensities are required, standard laser light sources at around 800 nm can be utilized in the microscopy experiments, and the excitation light is in the middle of the optical window where the penetration depth in tissue is maximal) with those of four-photon microscopy (a remarkably improved spatial resolution, such as 100 nm or below).

The molecular construct of the present disclosure allows for a true paradigm shift in multiphoton microscopy, since a spatial resolution equivalent to that offered by four-photon microscopy can be achieved without requiring the absorption of four photons. Instead, a two-photon absorbing probe can be utilized and the imaging can be performed with standard two-photon microscope equipment and laser as the irradiation source.

This allows for a quantum leap for the application in microscopy in biomedical contexts, such as diagnosis and evaluation of diseases or other clinical situations.

Most users of multiphoton microscopes cannot enjoy the superior resolution that the higher order excitations (three or four photon absorption) imply. No matter how carefully designed the molecular probe for two-photon microscopy is, the experiment is always limited by the fundamental law of photophysics; i.e. the emission intensity depends quadratically on the intensity of the excitation light, resulting in the $1/z^4$ resolution. The quadratic dependence of these molecules results from the mechanism of two-photon absorption: two photons are absorbed by the molecule such that the sum of the photon energies corresponds to the energy of the two-photon allowed electronic transition. As two photons are required to hit the molecule simultaneously, the probability (and rate) of photon absorption for each individual molecule depends quadratically on the photon flux. The molecular construct of the present disclosure obeys this law at the same time as it presents an innovative and unprecedented approach to circumvent this limitation by responding to the excitation light such that the concentration of the emissive species also depends quadratically on the intensity of the excitation light.

The molecular construct of the present disclosure comprises a two-photon absorbing probe (2PAP) linked to a photochromic molecule, which may also be referred to as a "molecular photoswitch". The two-photon absorbing probe (2PAP) may be covalently linked to the photochromic molecule.

The photochromic molecule can adopt a first, colored isomeric form (C) and a second, colorless form (CL).

The colored form can be isomerized to the colorless form by visible light (vis) in a one-photon process. Moreover, and central to the function of the proposed design, two-photon absorption triggers the same process.

The absorption spectrum of the first colored isomeric form (C) overlaps the emission spectrum of the two-photon absorbing probe (2PAP), which results in that the emission from the two-photon absorbing probe (2PAP) in the first configuration, 2PAP-C is being quantitatively quenched by the colored isomeric form (C) in a FRET reaction.

FRET (Fluorescence resonance energy transfer) is a distance-dependent interaction between two fluorophores. In FRET, a light source excites a donor fluorophore that transfers the energy to an acceptor fluorophore without emitting light. For an efficient FRET process to be accomplished, the donor and acceptor fluorophores must be close to one another. Furthermore, the emission spectrum of the donor fluorophore must overlap the absorption spectrum of the acceptor.

The FRET reaction does not only result in quenching of the 2PAP emission, but it also sensitizes the excitation of the colored isomeric form (C) of the photochromic molecule. As the fate of the colored isomeric form (C) does not depend on how it ended up in the excited state, FRET-sensitized isomerization to yield the second colorless isomeric form (CL) of the photochromic molecule follows. The absorption spectrum of the second colorless isomeric form (CL), however, does not overlap the emission spectrum of 2PAP, and FRET does not occur. Accordingly, in this isomeric form of the molecular construct (2PAP-CL), 2PAP emits intense fluorescence.

In embodiments, the two-photon absorbing probe (2PAP) is linked to the photochromic molecule such that the FRET efficiency of the molecular construct is at least 90%.

Accordingly, the two-photon absorbing probe (2PAP) is linked, and arranged sufficiently close in space, to the photochromic molecule to induce an efficient FRET process. Efficient FRET induced isomerization from the first, non-fluorescent configuration (2PAP-C) to the second, fluorescent configuration (2PAP-CL) can thereby be achieved.

The "FRET efficiency" is the ratio between the number of molecules that are deactivated by FRET and the number of molecules that are excited.

The first, non-fluorescent configuration (2PAP-C) is the thermodynamically stable form of the molecular construct.

In embodiments, the second colorless isomeric form (CL) of the photochromic molecule can be isomerized to the first colored isomeric form (C) by thermal isomerization. This may be referred to as "negative photochromism". In most photochromic molecules (photoswitches), the opposite applies; i.e. the colorless isomeric form is the thermally stable form.

In a "thermal" process, no photons are absorbed, and the process occurs without the involvement of photoexcitations. Instead, the thermal energy available is sufficient to drive the isomerization reaction.

Accordingly, the first, non-fluorescent configuration (2PAP-C) of the molecular construct can be switched to the second, fluorescent configuration (2PAP-CL) by means of photoisomerization. The second, fluorescent configuration (2PAP-CL) can be switched to the first, non-fluorescent configuration (2PAP-C) by means of thermal isomerization. This is an important feature of the molecular construct of the present disclosure.

In embodiments, the isomerization rate from the second, fluorescent configuration (2PAP-CL) to the first, non-fluorescent configuration (2PAP-C) is faster than the isomerization rate from the first, non-fluorescent configuration (2PAP-C) to the second, fluorescent configuration (2PAP-CL).

In other words, the thermal isomerization rate, $k_{therm}$ is faster than the two-photon FRET induced photoisomerization rate, $k_{photo}$. This condition allows for the concentration of the fluorescent form (2PAP-CL) to depend quadratically on the intensity of the excitation light. If this condition is not fulfilled, saturation of 2PAP-CL results such that conventional two-photon behavior is observed.

If $k_{therm}$ is substantially faster than the two-photon FRET induced photoisomerization rate, $k_{photo}$ the concentration of the fluorescent form (2PAP-CL) depends quadratically on the intensity of the excitation light. The emission intensity of each of these fluorescent species also depends quadratically on the intensity of the excitation light. This results in an overall quartic dependence of the emission intensity with the excitation intensity, that is, $I(em) \propto I(exc)^4$, which is normally only observed in four-photon microscopy. Accordingly, an improved spatial resolution and an improved imaging technique can be accomplished, that allows for significant improvements when applied in a multiphoton microscopy analysis.

In embodiments, the isomerization rate from the second, fluorescent configuration (2PAP-CL) to the first, non-fluorescent configuration (2PAP-C) (referred to above as $k_{therm}$) is at least 2 times faster, preferably at least 10 times faster, more preferably at least 50 times faster than the isomerization rate from the first, non-fluorescent configuration (2PAP-C) to the second, fluorescent configuration (2PAP-CL) (referred to as $k_{photo}$ above).

The absorption of two photons by the two-photon absorbing probe (2PAP) triggers the isomerization of the photochromic molecule, and thereby the switching of the first (non-fluorescent) configuration (2PAP-C) to the second (fluorescent) configuration (2PAP-CL). The absorption of two photons is not limited to light absorption in a particular range. However, typically, light of wavelengths in the range of from 700 to 900 nm is utilized in two-photon microscopy.

Accordingly, in embodiments, the two-photon absorbing probe (2PAP) absorbs light of wavelengths of at least 700 nm, preferably at wavelengths in the range of from 700 nm to 900 nm. This triggers the absorption of two photons.

In embodiments, the two-photon absorbing probe (2PAP) has a fluorescence quantum yield of at least 10%, preferably at least 30%, more preferably at least 50%.

As used herein, the term "fluorescence quantum yield" is the ratio between the number of photons emitted through fluorescence and the number of photons absorbed in a one-photon process. Accordingly, the quantum yield gives the probability of the excited state being deactivated by fluorescence rather than by another, non-radiative mechanism. In embodiments, the absorption spectrum of the first colored isomeric form (C) and the emission spectrum of the two-photon absorbing probe (2PAP) have a spectral overlap integral of at least $1 \times 10^{13}$ nm$^4$M$^{-1}$ cm$^{-1}$ Preferably, the spectral overlap integral is as high as possible to enable the fluorescent signal to be quenched in the FRET reaction (induced by two photon absorption). This reduces the "noise" and undesired emission of fluorescence in the 2PAP-C; i.e. the intended non-fluorescent configuration of the molecular construct.

In embodiments, the photochromic molecule has a thermal half-life ($t_{1/2}$) of less than 20 seconds, preferably less than 10 seconds, more preferably less than 1 second, at room temperature. This is to ensure that the concentration of the fluorescent form (2PAP-CL) is kept low at all times in order for the concentration of 2PAP-CL to depend quadratically on the excitation intensity.

In embodiments, the colored form of the photochromic molecule (C) absorbs light within the wavelength region from 350 to 800 nm, preferably from 450 to 700 nm.

The ability of the photochromic molecule to absorb in these wavelength regions allows for efficient FRET to occur from the two-photon absorbing probe, 2PAP, to the first colored isomeric form (C) of the photochromic molecule, and for conventional lasers to be used as the excitation source.

According to another aspect, there is provided a method for analyzing a target structure in a multiphoton microscope comprising the steps of:
a) incubating a molecular construct as described hereinbefore with a target structure to provide a fluorescently labeled target structure,
b) irradiating the fluorescently labeled target structure with light in a wavelength range that enables two-photon absorption by the molecular construct such that a fluorescent signal is generated, and
c) detecting and/or measuring the fluorescent signal.

The target structure to be analyzed may e.g. be fixed or live cells, tissue samples, biological samples, such as body fluids, and various 3D structures etc.

The molecular construct may be incubated with the target structure by means known to the skilled person.

Typically, the target structure is irradiated with light having a wavelength of at least 700 nm. This allows for two photon absorption to occur, which then triggers a set of events, wherein the molecular construct becomes fluorescent. Furthermore, the fluorescence is expected to yield a spatial resolution equivalent to what is observed in a four-photon microscopy.

The emitted fluorescence may be detected and/or quantitatively measured by means known to the skilled person. Accordingly, the properties of the target structure can by analyzed in great detail and with an enhanced spatial resolution.

According to another aspect, there is provided an antibody tagged with the molecular construct as described hereinbefore.

Such antibodies may be efficiently used to detect specific target regions in a cell, tissue or body fluid. Antibodies targeted towards specific antigens provide a useful approach in which the molecular construct of the present disclosure can reveal important information on the etiology of specific diseases and biological pathways.

Preferably, the antibody is a monoclonal antibody.

According to yet another aspect, the present disclosure relates to the use of a molecular construct as described hereinbefore for imaging a target structure in a multiphoton microscope, e.g. a two-photon microscope.

Further features of, and advantages with, the present disclosure will become apparent when studying the appended claims and the following description. The skilled addressee realizes that different features of the present disclosure may be combined to create embodiments other than those described in the following, without departing from the scope of the present disclosure.

BRIEF DESCRIPTION OF THE DRAWINGS

The various aspects of the present disclosure, including its particular features and advantages, will be readily understood from the following detailed description and the accompanying drawings, in which.

DETAILED DESCRIPTION

The present disclosure will now be described more fully hereinafter with reference to the accompanying drawings, in which currently preferred embodiments of the present disclosure are shown. The present disclosure may, however, be embodied in many different forms and should not be construed as limited to the embodiments set forth herein; rather, these embodiments are provided for thoroughness and completeness, and fully convey the scope of the present disclosure to the skilled person.

Figure 1:
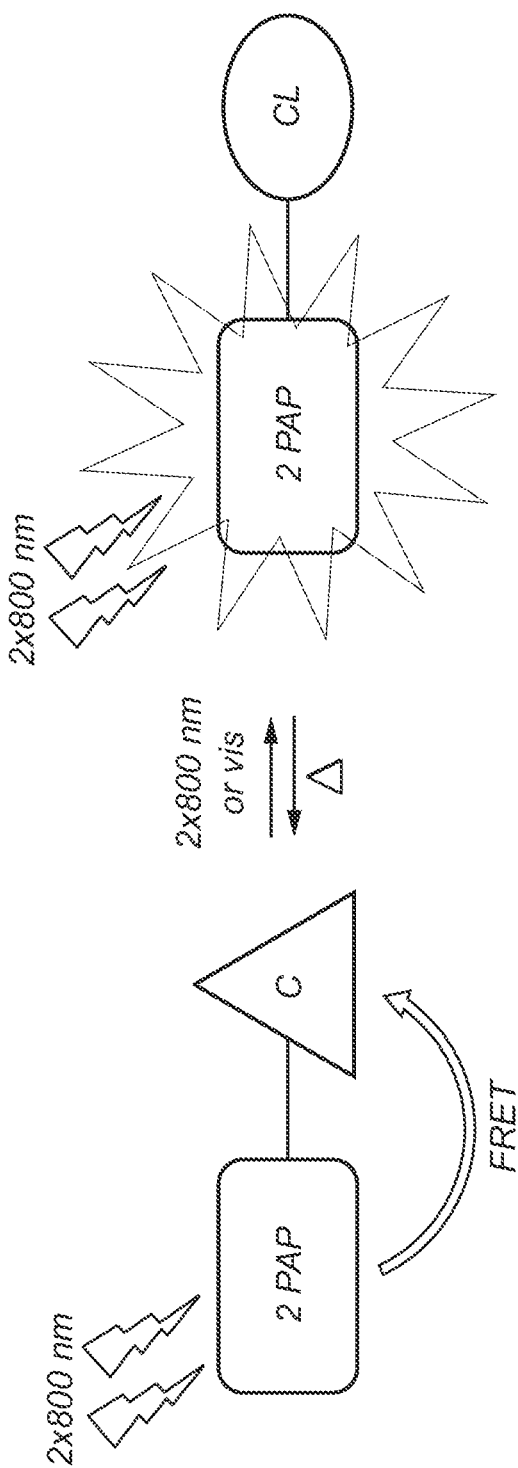
FIG. 1 schematically discloses the molecular construct of the present disclosure and its mode of action.

FIG. 1 schematically illustrates a molecular construct of the present disclosure. The two-photon excitation process is indicated by the 2×800 nm photons.

2PAP-C represents the first, non-fluorescent configuration of the molecular construct, and 2PAP-CL represents the second, fluorescent configuration. 2PAP-C is the thermodynamically stable form of the molecular construct.

The molecular construct comprises a two-photon absorbing probe (2PAP) linked to a photochromic molecule, which can adopt a first colored isomeric form (C) and a second colorless isomeric form (CL).

The two-photon absorbing probe (2PAP) is typically covalently linked to the photochromic molecule.

When two photons are absorbed simultaneously by 2PAP, which may occur by e.g. irradiating the molecular construct with an irradiation source, such as laser, 2PAP is excited to the lowest excited singlet state.

The absorption spectrum of C overlaps the emission spectrum of 2PAP resulting in that the emission from 2PAP in 2PAP-C is being efficiently quenched by C in a FRET reaction. The FRET reaction does not only result in quenching of the 2PAP emission, but it also sensitizes the excitation of C. As the fate of C does not depend on how it ended up in the excited state, FRET-sensitized isomerization to yield CL follows. The absorption spectrum of CL does not overlap the emission of 2PAP, and accordingly, FRET does not occur. This implies that in this isomeric form of the molecular construct (2PAP-CL), 2PAP emits intense fluorescence.

Hence, the effect of the intensity of the light (arbitrarily set to 800 nm in FIG. 1) used to excite 2PAP in a two-photon process is twofold. First, the fluorescence intensity of 2PAP in each individual fluorescent isomer (2PAP-CL) depends quadratically on the excitation intensity. Second, the concentration of the fluorescent isomer 2PAP-CL also depends quadratically on the excitation intensity. This is because the rate of the FRET-sensitized isomerization from the non-fluorescent form 2PAP-C to the fluorescent form 2PAP-CL depends on the rate at which 2PAP in 2PAP-C absorbs photons. This rate depends quadratically on the intensity of the excitation light.

Accordingly, both the fluorescence intensity "per fluorescent molecule" as well as the concentration of the fluorescent molecules depend quadratically on the excitation intensity. This results in an overall quartic dependence of the fluorescence intensity: $I(em) \propto I(exc)^4$. Particularly, this applies if the thermal isomerization rate from the fluorescent form 2PAP-CL to the non-fluorescent form 2PAP-C is significantly faster than the two-photon FRET-induced isomerization from 2PAP-C to 2PAP-CL. In FIG. 1, the thermal isomerization is denoted A.

Figure 2:
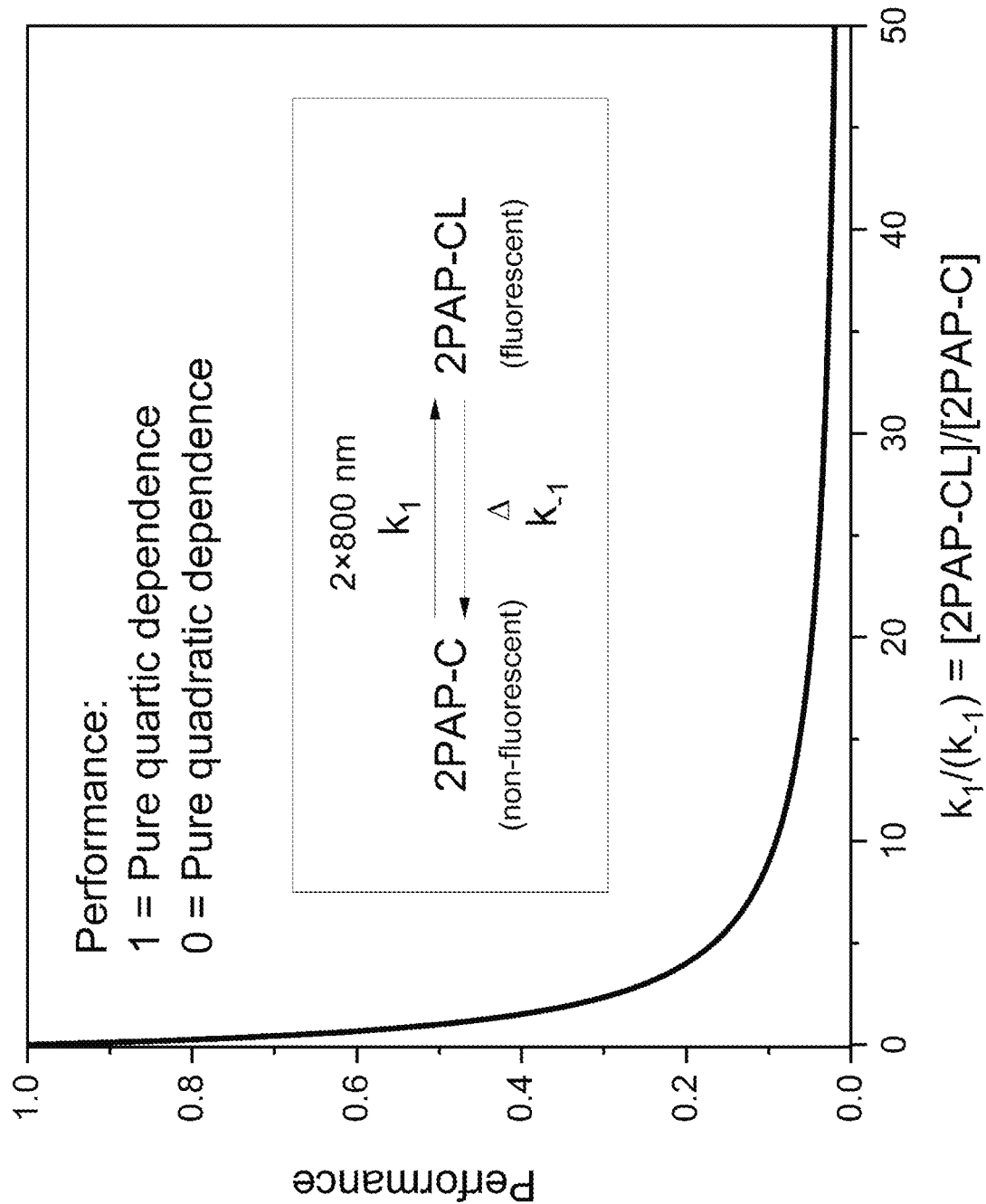
FIG. 2 is a performance plot illustrating the four-photon behavior of the molecular construct of the present disclosure.

In FIG. 2, the principles of the performance of the design of the present disclosure is schematically outlined. The general principle of the design is that the two-photon-induced FRET-sensitized photoisomerization is delicately balanced with thermal isomerization such that the emitted fluorescence intensity displays a quartic dependence on the excitation intensity. $k_1$ and $k_{-1}$ in FIG. 2 correspond to $k_{photo}$, and $k_{therm}$, discussed above, respectively. FIG. 2 shows that a perfect four-photon behavior (quartic dependence) is observed when $k_1/k_{-1}$ is close to zero (very low concentration of the fluorescent form 2PAP-CL). This implies that an improved spatial resolution can be obtained with the molecular construct of the present disclosure.

Figure 3:
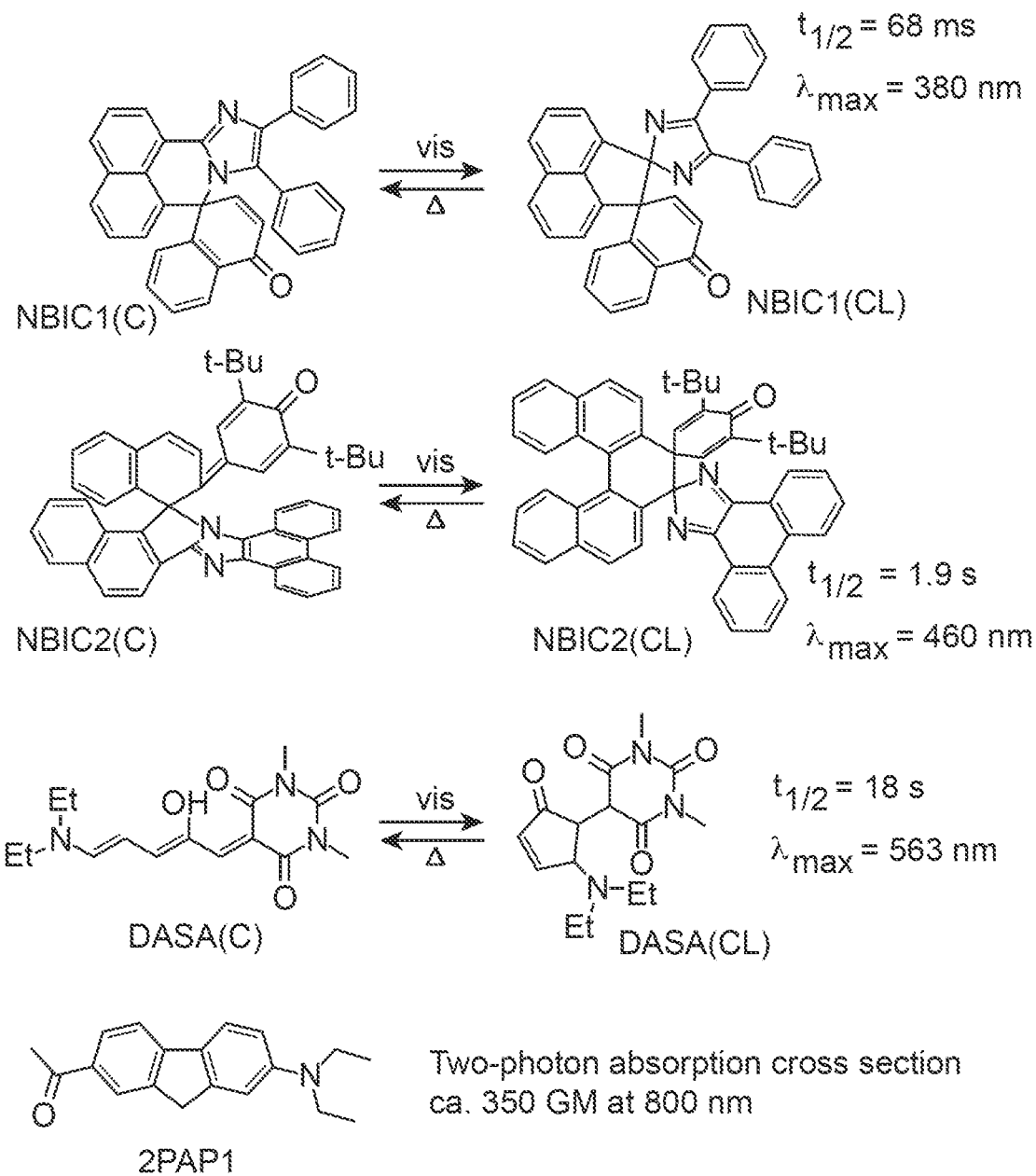
FIG. 3 illustrates examples of photochromic molecules that can be used in a molecular construct of the present disclosure.

FIG. 3 illustrates examples of photochromic molecules; i.e. photoswitches that can be used in the molecular construct of the present disclosure. These molecules fulfill the "negative photochromism" feature of the molecular construct of the present disclosure. The isomerization schemes are also illustrated. $t_{1/2}$ denotes the thermal half-lives and correspond to the thermal isomerization to the colored form of the photochromic molecule at 25° C. $\lambda_{max}$ indicates the wavelength maximum of the most redshifted absorption band for the colored isomeric form (C). A potential, and exemplary 2PAP derivative is also shown in FIG. 3.

It should be noted that the molecular construct of the present disclosure is by no means limited to a specific two photon absorbing probe, but any 2PAP that can be linked to a photochromic molecule can be utilized. A preferred 2PAP for use in the molecular construct of the present disclosure has a fluorescence quantum yield of at least 10%, preferably at least 30%, more preferably at least 50%.

Figure 4:
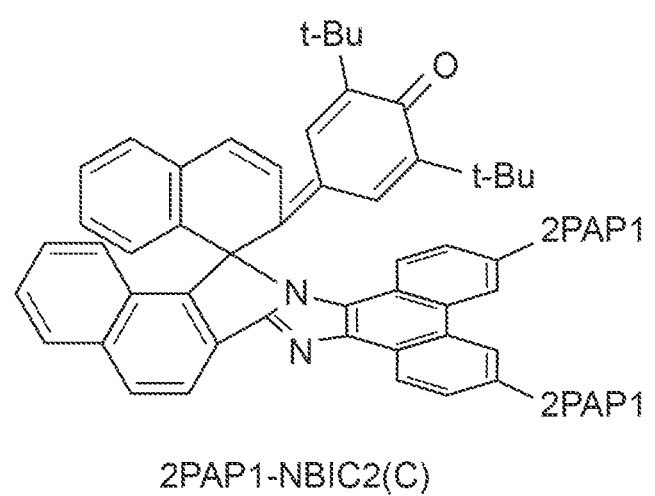
FIG. 4 schematically illustrates how the two-photon absorbing probe (2PAP) can be linked to an exemplary photochromic molecule.

FIG. 4 schematically illustrates an exemplary molecular construct of the present disclosure, wherein 2PAP is linked to a photochromic molecule.

The present disclosure is by no means limited to the use of a particular photochromic molecule. Any photochromic molecule having the ability to display negative photochromism can be used; i.e. any photochromic molecule having the ability to be switched from a colorless isomeric form to a colored isomeric by thermal isomerization can be used.

In preferred embodiments, the photochromic molecule has a thermal half-life ($t_{1/2}$) of less than 20 seconds, preferably less than 10 seconds, more preferably less than 1 second, at room temperature.

Terms, definitions and embodiments of all aspects of the present disclosure apply mutatis mutandis to the other aspects of the present disclosure.

Even though the present disclosure has been described with reference to specific exemplifying embodiments thereof, many different alterations, modifications and the like will become apparent for those skilled in the art.

Variations to the disclosed embodiments can be understood and effected by the skilled addressee in practicing the present disclosure, from a study of the drawings, the disclosure, and the appended claims. Furthermore, in the claims, the word "comprising" does not exclude other elements or steps, and the indefinite article "a" or "an" does not exclude a plurality.

The invention claimed is:

1. A molecular construct for multiphoton fluorescence microscopy imaging, wherein said molecular construct has a first, non-fluorescent configuration (2PAP-C) and a second, fluorescent configuration (2PAP-CL), wherein said molecular construct comprises:
   a two-photon absorbing probe (2PAP) having an emission spectrum, and
   a photochromic molecule linked to the two-photon absorbing probe (2PAP), wherein said photochromic molecule has a first colored isomeric form (C) and a second colorless isomeric form (CL), wherein said first colored isomeric form (C) has a first absorption spectrum that overlaps the emission spectrum of said two-photon absorbing probe (2PAP) such that the first colored isomeric form (C) photoisomerizes to said second colorless isomeric form (CL) upon absorption of two photons by said two-photon absorbing probe (2PAP), wherein of said second colorless isomeric form (CL) has a second absorption spectrum that does not overlap said emission spectrum of said two-photon absorbing probe (2PAP), and wherein said second colorless isomeric form (CL) isomerizes to said first colored isomeric form (C) by thermal isomerization.

2. The molecular construct according to claim 1, wherein said two-photon absorbing probe (2PAP) is linked to said photochromic molecule such that the FRET efficiency of said molecular construct is at least 90%.

3. The molecular construct according to claim 1, wherein said first, non-fluorescent configuration (2PAP-C) is the thermodynamically stable form of said molecular construct.

4. The molecular construct according to claim 1, wherein the rate of the thermal isomerization from said second, fluorescent configuration (2PAP-CL) to said first, non-fluorescent configuration (2PAP-C) is faster than the rate of the photoisomerization from said first, non-fluorescent configuration (2PAP-C) to said second, fluorescent configuration (2PAP-CL).

5. The molecular construct according to claim 4, wherein the rate of the thermal isomerization rate from said second, fluorescent configuration (2PAP-CL) to said first, non-fluorescent configuration (2PAP-C) is at least 2 times faster than the rate of the photoisomerization from said first, non-fluorescent configuration (2PAP-C) to said second, fluorescent configuration (2PAP-CL).

6. The molecular construct according to claim 1, wherein said two-photon absorbing probe (2PAP) absorbs light of wavelengths of at least 700 nm.

7. The molecular construct according to claim 1, wherein said two-photon absorbing probe (2PAP) has a fluorescence quantum yield of at least 10%.

8. The molecular construct according to claim 1, wherein the absorption spectrum of said first colored isomeric form (C) and the emission spectrum of said two-photon absorbing probe (2PAP) have a spectral overlap integral of at least $1 \times 10^{13} mn^4 M^{-1} cm^{-1}$.

9. The molecular construct according to claim 1, wherein said photochromic molecule has a thermal half-life ($t_{1/2}$) of less than 20 seconds at room temperature.

10. The molecular construct according to claim 1, wherein said photochromic molecule absorbs light within the wavelength region of from 350 to 800 nm.

11. The molecular construct according to claim 4, wherein the rate of the thermal isomerization rate from said second, fluorescent configuration (2PAP-CL) to said first, non-fluorescent configuration (2PAP-C) is at least 10 times faster than the rate of the photoisomerization from said first, non-fluorescent configuration (2PAP-C) to said second, fluorescent configuration (2PAP-CL).

12. The molecular construct according to claim 4, wherein the rate of the thermal isomerization rate from said second, fluorescent configuration (2PAP-CL) to said first, non-fluorescent configuration (2PAP-C) is at least 50 times faster than the rate of the photoisomerization from said first, non-fluorescent configuration (2PAP-C) to said second, fluorescent configuration (2PAP-CL).

13. The molecular construct according to claim 1, wherein said two-photon absorbing probe (2PAP) absorbs light of wavelengths in the range of from 700 nm to 900 nm.

14. The molecular construct according to claim 1, wherein said two-photon absorbing probe (2PAP) has a fluorescence quantum yield of at least 30%.

15. The molecular construct according to claim 1, wherein said two-photon absorbing probe (2PAP) has a fluorescence quantum yield of at least 50%.

16. The molecular construct according to claim 1, wherein said photochromic molecule has a thermal half-life ($t_{1/2}$) of less than 10 seconds at room temperature.

17. The molecular construct according to claim 1, wherein said photochromic molecule absorbs light within the wavelength region of from 450 nm to 700 nm.

18. An antibody tagged with the molecular construct according to claim 1.

19. A method for analyzing a target structure in a sample in a multiphoton microscope comprising the steps of:
    a) incubating the molecular construct according to claim 1 with the target structure to provide a fluorescently labeled target structure,
    b) irradiating said fluorescently labeled target structure with light in a wavelength range that enables two-photon absorption by said molecular construct such that a fluorescent signal is generated, and
    c) detecting and/or measuring said fluorescent signal.

20. The method according to claim 19, wherein said fluorescently labeled target structure is irradiated with light having a wavelength of at least 700 nm.

* * * * *